(12) United States Patent
Wodnicki et al.

(10) Patent No.: US 7,892,176 B2
(45) Date of Patent: Feb. 22, 2011

(54) MONITORING OR IMAGING SYSTEM WITH INTERCONNECT STRUCTURE FOR LARGE AREA SENSOR ARRAY

(75) Inventors: Robert Gideon Wodnicki, Niskayuna, NY (US); David Martin Mills, Niskayuna, NY (US); Rayette Ann Fisher, Niskayuna, NY (US); Charles Gerard Woychik, Nishkayuna, NY (US)

(73) Assignee: General Electric Company, Niskayuna, NY (US)

( * ) Notice: Subject to any disclaimer, the term of this patent is extended or adjusted under 35 U.S.C. 154(b) by 813 days.

(21) Appl. No.: 11/743,391

(22) Filed: May 2, 2007

(65) Prior Publication Data
US 2008/0273424 A1    Nov. 6, 2008

(51) Int. Cl.
  A61B 8/14 (2006.01)
(52) U.S. Cl. .............................. 600/459; 257/E27.006
(58) Field of Classification Search ................. 257/443, 257/444, 416, E25.013; 600/437, 459; 310/334; 367/174
  See application file for complete search history.

(56) References Cited

U.S. PATENT DOCUMENTS

| | | | |
|---|---|---|---|
| 5,329,498 A * | 7/1994 | Greenstein | 367/155 |
| 5,732,706 A | 3/1998 | White et al. | |
| 5,834,843 A * | 11/1998 | Mori et al. | 257/723 |
| 6,013,032 A | 1/2000 | Savord | |
| 6,282,963 B1 | 9/2001 | Haider | |
| 6,346,079 B1 | 2/2002 | Haider et al. | |
| 6,491,634 B1 | 12/2002 | Leavitt et al. | |
| 6,506,160 B1 * | 1/2003 | Van Stralen et al. | 600/459 |
| 6,541,896 B1 | 4/2003 | Piel, Jr. et al. | |

(Continued)

FOREIGN PATENT DOCUMENTS

WO  PCT/IB2005/053803    11/2005

(Continued)

OTHER PUBLICATIONS

U.S. Appl. No. 11/172,599, filed Jun. 29, 2005, Thomenius et al.

(Continued)

*Primary Examiner*—Minh-Loan T Tran
*Assistant Examiner*—Vongsavanh Sengdara
(74) *Attorney, Agent, or Firm*—Jason K. Klindtworth (57) ABSTRACT

An ultrasonic monitoring system is formed with a probe unit. In one example an array of transducer cells is arranged in rows and columns formed along a first plane with a first pitch along a first direction. An integrated circuit including an array of circuit cells is formed along a second plane parallel to the first plane. The circuit cells are spaced apart along the first direction at a second pitch smaller than the first pitch. A first of the transducer cells is vertically aligned, along a direction normal to one of the planes, with a first of the circuit cells and having a connection thereto. A second of the transducer cells is offset from vertical alignment with respect to the position of a second circuit cell so as to not overlie the second circuit cell. A connection subsystem is positioned between the array of transducer cells and the array of circuit cells, configured to form connection of the first transducer cell to the first circuit cell and connection of the second transducer cell with the second circuit cell.

24 Claims, 8 Drawing Sheets

U.S. PATENT DOCUMENTS

| | | |
|---|---|---|
| 6,589,180 B2 | 7/2003 | Erikson |
| 6,865,140 B2 | 3/2005 | Thomenius et al. |
| 7,052,464 B2 | 5/2006 | Wodnicki |
| 7,053,530 B2 | 5/2006 | Baumgartner et al. |
| 2001/0043090 A1 | 11/2001 | Savord |
| 2004/0113524 A1 | 6/2004 | Baumgartner et al. |
| 2005/0094490 A1 | 5/2005 | Thomenius et al. |
| 2005/0096546 A1 | 5/2005 | Hazard et al. |
| 2006/0118939 A1 | 6/2006 | Fisher et al. |
| 2006/0133198 A1* | 6/2006 | Fisher et al. ............ 367/13 |
| 2007/0016026 A1 | 1/2007 | Thomenius et al. |
| 2008/0183078 A1 | 7/2008 | Haider et al. |

FOREIGN PATENT DOCUMENTS

| | | |
|---|---|---|
| WO | WO 2006/054260 | 5/2006 |
| WO | WO 2006/075283 A2 | 7/2006 |
| WO | WO 2006/131875 A2 | 12/2006 |

OTHER PUBLICATIONS

Wygant, Ira O. "A Miniature Real-Time Volumetric Ultrasound Imaging System", Proc. of SPIE vol. 5750, pp. 26-36, 2005.

Beyne, E. "The Rise of the 3rd Dimension for System Integration", Interconnect Technology Conference, 2006 International, Jun. 5-7, 2006 Page(s): 1-5.

Fisher, R. et al. "Reconfigurable Arrays for Portable Ultrasound", Ultrasonics Symposium, 2005 IEEE, vol. 1, Sep. 18-21, 2005 pp. 495-499.

Brunner, Eberhard. "Ultrasound System Considerations and their Impact on Front-End Components", Analog Devices, Inc. 2002.

* cited by examiner

MONITORING OR IMAGING SYSTEM WITH INTERCONNECT STRUCTURE FOR LARGE AREA SENSOR ARRAY

STATEMENT REGARDING FEDERALLY SPONSORED RESEARCH & DEVELOPMENT

This invention was made with Government support under contract number 1 RO1 EB002485-01, awarded by National Institute of Health. The Government has certain rights in the invention.

BACKGROUND OF THE INVENTION

1. Field of the Invention

This invention relates generally to large area array monitoring or imaging systems of the type used for ultrasound or x-ray analysis and, more particularly, to systems and methods which combine high density transducer arrays with processing circuitry.

2. Background Art

Ultrasound monitoring and imaging systems use transducer arrays to create short high frequency acoustic pulses which undergo reflection from surface interfaces at which there are changes in acoustic impedance. The transducers convert reflected energy into electrical signals which are processed to generate two-dimensional or three-dimensional image information descriptive of a subject under study.

Acoustic transducer cells are typically multi-layered structures comprising piezoelectric or micro-machined transducers configured with electronic circuitry in a probe assembly. The electrical signals are further processed by beam forming circuitry, typically external to the probe assembly, to generate and display images of structures being studied.

It is desirable for ultrasound probes to contain a portion of the beam forming circuitry integrated with the transducer array, as this can reduce complexities and potentially adverse effects which may result from connecting cables between the transducer probe and an external system that provides signal processing and control functions. For example, with connecting cables extending over distances on the order of several meters significant capacitance effects can arise. Furthermore, signals received from the transducer assembly may be weak, subject to RF interference and may exhibit an undesirably low S/N ratio. To mitigate these effects, front-end circuit cells providing, for example, amplification, pulse generation, and transmit/receive switching, can be integrated with a transducer array.

Transducer arrays in ultrasound probe assemblies typically span an area of about 20 $cm^2$. For new medical applications, such as screening for internal bleeding and tumors, much larger arrays, on the order of 300 $cm^2$, are required. In non-medical applications even larger arrays may be desired.

Such large arrays may be formed by tiling of a large number of transducer modules in rows and columns. Each transducer module comprises a subarray of transducer cells and an integrated circuit coupled to the subarray. Performance of large transducer area is significantly degraded when there are significant variations in spacings between modules.

BRIEF DESCRIPTION OF THE INVENTION

In one form of the invention, an ultrasonic monitoring system is formed with a probe unit having an array of transducer cells arranged in rows and columns and formed along a first plane with a first pitch along a first direction. An integrated circuit including an array of circuit cells is formed along a second plane parallel to the first plane. The circuit cells are spaced apart along the first direction at a second pitch smaller than the first pitch. A first of the transducer cells is vertically aligned, along a direction normal to one of the planes, with a first of the circuit cells and having a connection thereto, and a second of the transducer cells is offset from vertical alignment with respect to the position of a second circuit cell so as to not overlie the second circuit cell. A connection subsystem is positioned between the array of transducer cells and the array of circuit cells, configured to form the connection of the first transducer cell to the first circuit cell and to connect the second transducer cell with the second circuit cell. An interconnection structure is positioned to provide electrical connections between the integrated circuit 106 and processing circuitry.

A method of forming an ultrasonic imaging system having transducer circuitry includes providing an array of transducer cells along a first plane with a first pitch along a first direction, and providing an integrated circuit device comprising an array of circuit cells and comprising a plurality of I/O pads formed along an edge of the device. The circuit cells are formed along the first direction with a second pitch smaller than the first pitch, with a first of the cells overlying a first circuit cell along a direction normal to the first plane, for connection thereto, and with a second transducer cell offset with respect to the positions of the first transducer cell and the first circuit cell so as not to overlie the second circuit cell. A redistribution system is configured to route a connection between the second cell and the second circuit cell. An interconnection structure is provided which comprises an array of connectors. The connectors provide connections between I/O pads of integrated circuit structures in a plurality of transducer modules and electronic components of an ultrasonic imaging system.

BRIEF DESCRIPTION OF THE DRAWINGS

The invention will be more clearly understood from the following description wherein an embodiment is illustrated, by way of example only, with reference to the accompanying drawings, in which.

Like reference numbers are used throughout the figures to indicate like features. Individual features in the figures may not be drawn to scale.

DETAILED DESCRIPTION OF THE INVENTION

Figure 1:
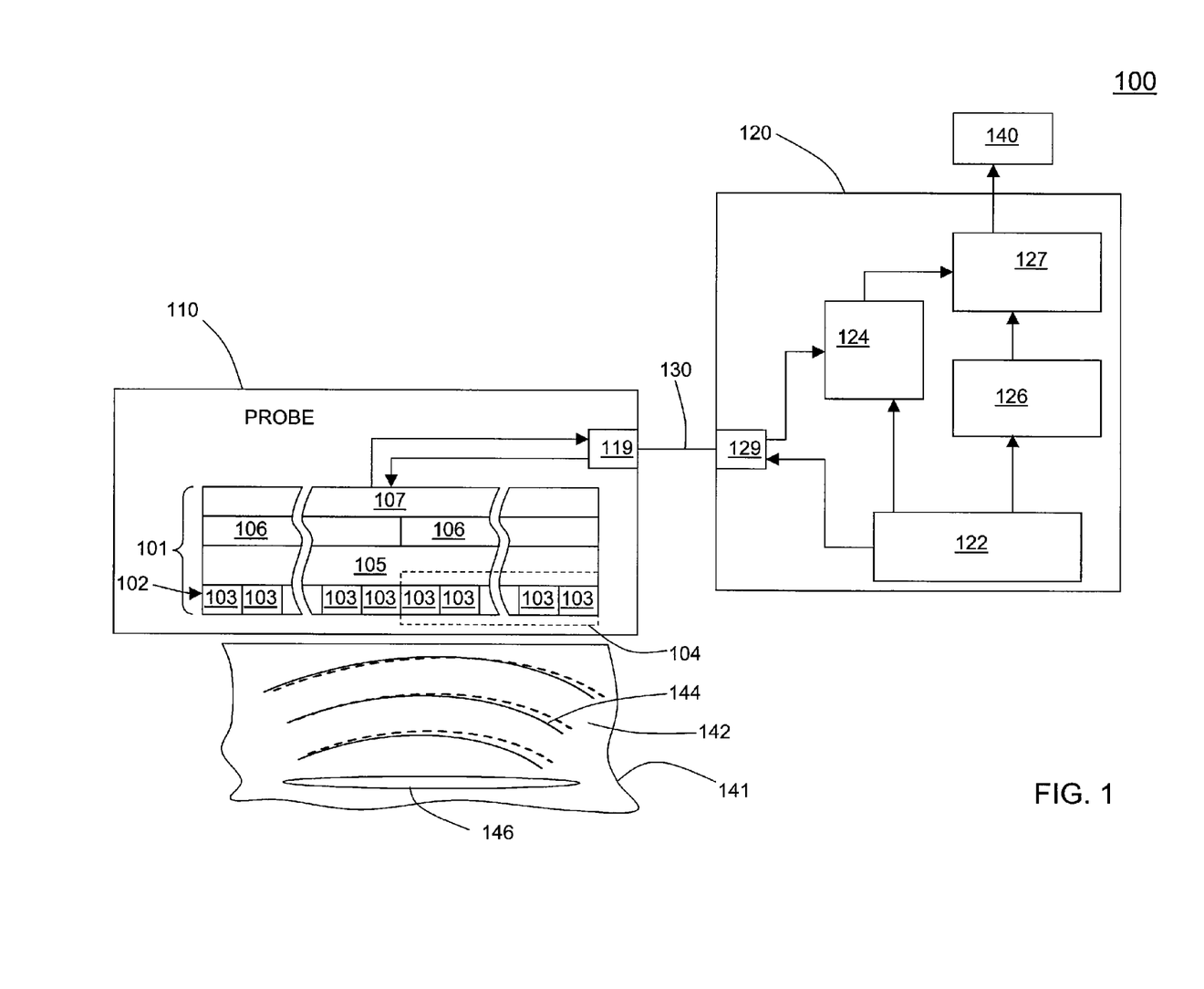
FIG. 1 is a block diagram of an ultrasound imaging system.

FIG. 1 illustrates an exemplary ultrasound monitoring system 100, in this example, one of the type used for medical imaging, having a probe unit that is relatively light and suitable for hand-held use. More generally, embodiments of the invention include, but are not limited to, acoustic monitoring or imaging systems which, generally, incorporate large arrays of transducers.

The system 100 includes a probe unit 110 connected to a system console 120 by a multi-channel cable 130 and a display 140 connected to the console 120. The probe unit 110 comprises a transducer assembly 101 having an array 102 of transducer cells 103, a connector 105, a plurality of Application Specific Integrated Circuits (ASICs) 106, and an interconnection structure 107. The console 120 includes a system controller 122, a main beamformer 124, an image processor 126, and a scan converter 127. The transducer cell array 102 includes a plurality of transducer subarrays 104, each containing a like number of transducer cells 103 arranged in columns and rows. Exemplary transducer subarrays 104 are illustrated in the plan view of FIG. 2. Each subarray 104 is coupled to a corresponding Application Specific Integrated Circuit (ASIC) 106 through the connector 105. The term processing circuitry, as used herein, refers to various types of analog or digital circuitry which perform signal processing functions common to imaging and monitoring systems including the system 100. For example, circuitry placed in the probe unit or in the system console, e.g., the image processor, is to be understood to include processing circuitry supportive of functions such as amplification, filtering, beam forming or image processing. Although illustrated embodiments specify locations for such circuitry, this is not at all limiting. Circuitry placed in the system console may be partly or entirely integrated within the probe unit, and circuitry in the probe unit may be positioned in a console. Moreover, some embodiments which incorporate the invention may not require a console.

The interconnection structure 107 is coupled to send and receive signals between the ASICs 106, each associated with one of the transducer subarrays 104, and circuitry, e.g., processing circuitry, in the system console 120. According to the embodiments of FIGS. 3-7, the assembly 101 includes a large number of ASICs 106, each connected to a corresponding subarray 104 having a large number of transducer cells 103. Information is transferred between the probe unit 110 and the system console 120 via the cable 130 which is coupled between a probe unit line connector 119 in the probe unit 110 and a console line connector 129 in the system console 120.

In the system console 120, the system controller 122 is coupled to the main beamformer 124, the image processor 126, and the ASICs 106 in the probe unit 110 to provide necessary timing signals for operation of the system 100. Each ASIC 106 provides electronic transmit signals to a transducer subarray 104 to generate ultrasonic pressure waves herein illustrated by ultrasound lines 142, which may return to the array as reflections 144 from an area of investigation 146 in an object 141 under study. The main beamformer 124 is coupled to the scan converter 127 to form an image for the display 140.

Figure 2:
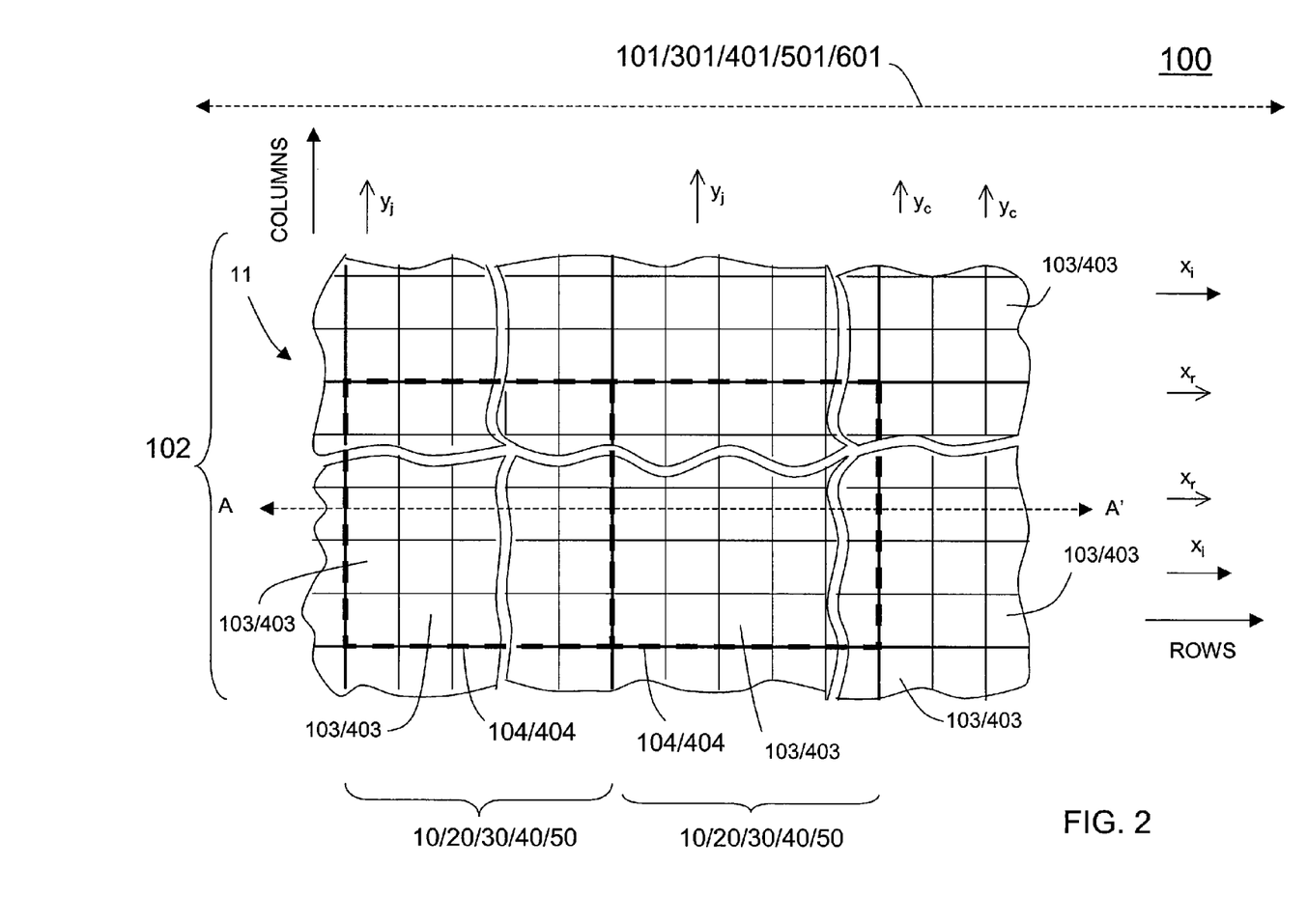
FIG. 2 illustrates in a partial plan view a large area array transducer assembly.

The plan view of FIG. 2 illustrates a transducer assembly 101 of in the ultrasound imaging system 100, comprising a large number of transducer modules 10 formed in an array 11 along rows xi and columns yj of the assembly 101. The transducer assembly 101 is functionally interchangeable with any one of the transducer assemblies 301, 401, 501, and 601 illustrated in FIGS. 4-7 and the module 10 is functionally interchangeable with any one of the modules 20, 30, 40, and 50 in FIGS. 4-7. The transducer cells 103 are functionally interchangeable with a transducer cells shown in other embodiments and the subarrays 104 are functionally interchangeable with subarrays shown in other embodiments.

Each module 10 comprises a subarray 104 of transducer cells 103 having the cells 103 arranged in rows xr and columns yc such that the subarrays 104, together, form the large array 102 having all of the transducer cells 103 arranged along the rows xr and columns yc. The rows xr and columns yc and the modules 10 extend along a plane P11 (shown in FIG. 3) and, in some embodiments, all of the cells 103 are positioned in the same plane. In other embodiments the cells may form an array having curvature with respect to the plane P11. Each module 10, comprising a transducer subarray 104 and a corresponding ASIC 106 is coupled to the interconnection structure 107 to form the transducer assembly 101.

Figure 3:
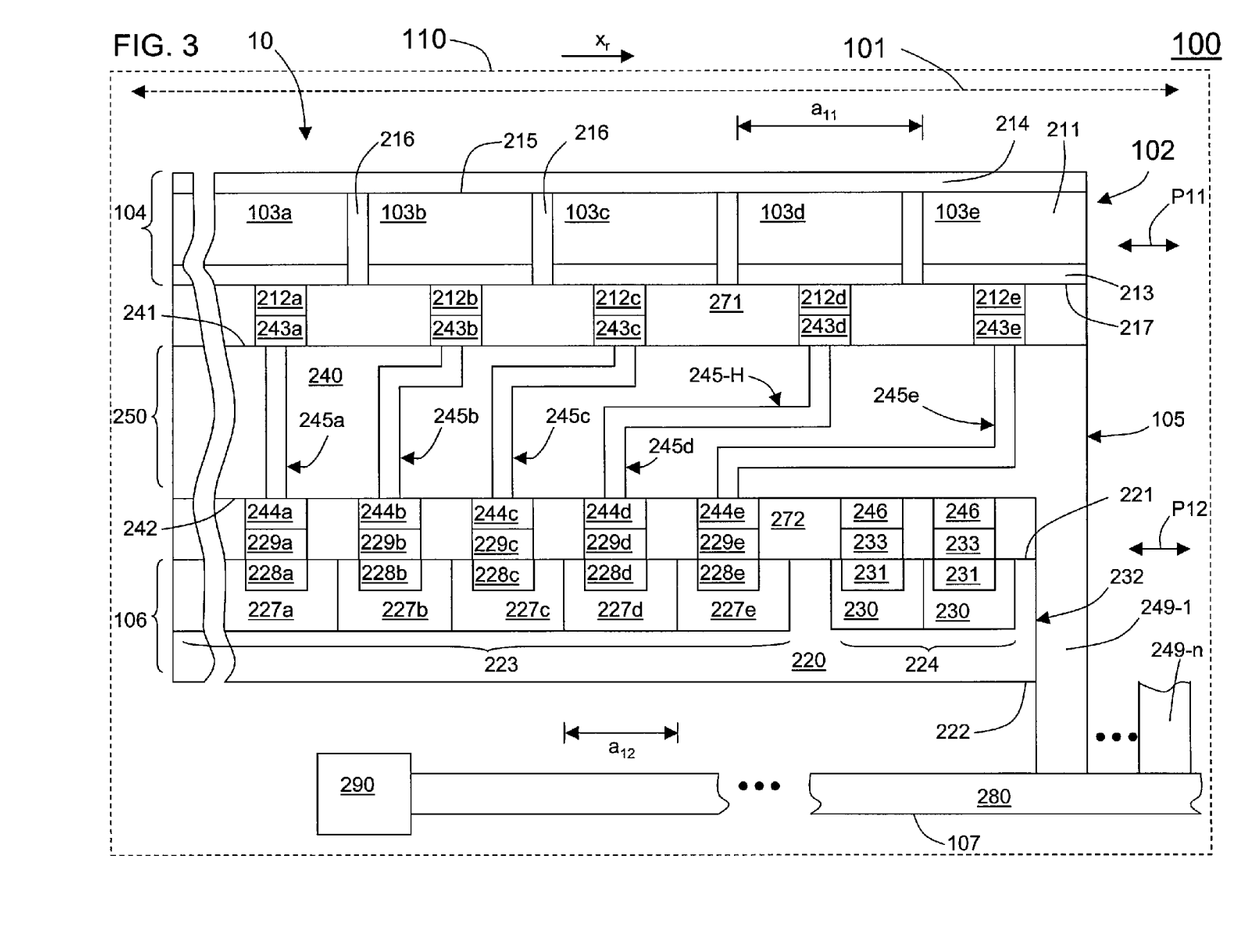
FIG. 3 illustrates in cross-sectional view the large area array transducer assembly of FIG. 2.

Referring to the partial cross-sectional view of FIG. 3, taken along the line A-A' of FIG. 2, an exemplary transducer module 10 in the transducer assembly 101 is shown. Each module 10 comprises a subarray 104 of transducer cells 103 having the cells 103 arranged in rows $x_r$ and columns $y_c$ such that the subarrays 104, together, form the larger array 102 having all of the transducer cells 103 arranged along the rows $x_r$ and columns $y_c$. The rows $x_r$ and columns $y_c$ and the modules 20 extend along the plane P11 and, in some embodiments, all of the cells 103 are positioned in the same plane. Each module 10, comprising a transducer subarray 104 and a corresponding Application Specific Integrated Circuit (ASIC) 106, is coupled to the interconnection structure 107 to form the transducer assembly 101 as shown in FIG. 1.

Each module 10 includes the transducer subarray 104, the ASIC 106 having a plurality of transducer circuit cells 227 (e.g., 227a-227e), and a connector 105 serving as a circuit connection interface between individual transducer cells 103 in the sub-array 104 and the corresponding circuit cell 227 in the ASIC 106. The connector 105 may, as illustrated, be a flexible circuit assembly 240, having a plurality of upper flex contact pads 243 (e.g, 243a-243e) formed along an upper surface 241 and a plurality of lower flex contact pads 244 (e.g, 244a-244e) formed along a lower surface 242 and a plurality of conductive paths 245 (e.g., 245a-245e) connecting pairs of pads 243 and 244; and further including a flexible connector portion, herein referred as a flex tail 249-1. The connector 105 may also provide electrical connections for one or more other ASICs adjacent the illustrated ASIC 106.

The transducer cells 103 in each subarray 104 are wired through the connector 105 to the ASIC 106 in the module 10. An array of transducer modules 10 may be connected to the interconnection structure 107 formed of a rigid substrate 280, for example, a printed circuit board. That is, multiple flex tails 249-1 to 249-$n$ may provide the connection interface between one of the modules 10 and the substrate 280 of the interconnection structure 107. The flex tails may incorporate a standard circuit board connectors, flex pressure connectors, an anisotropically conductive film (ACF), or any other connection mechanism to effect attachment to the interconnection structure 107. The structure 107 is coupled to an assembly connector portion 290 for transmitting signals to and receiving signals from the system console 120 (shown in FIG. 1).

In each transducer cell 103 the transducer component 211 comprises a piezoelectric material such as lead zirconate titanate (PZT) formed over a lower or rear electrode 213 which is connected to an associated transducer contact pad 212 (e.g., one of 212a-212e) formed along a lower surface 217 of the rear electrode 213. A front electrode 214 is a thin conductive material deposited over the upper surface 215 of the entire transducer subarray 104 which may provide a common ground electrode for all of the transducer cells 103 in the module 10. In addition to the piezoelectric material, each transducer component 211 may further comprise one or more matching layers (not shown) which provide suitable acoustic characteristics for transmitting acoustic signals to and receiving acoustic signals from an object under study. The common ground may be formed among the matching layers instead of or in addition to being positioned on top of the piezoelectric material, e.g., with a front electrode. Each rear electrode 213 and transducer component 211 is electrically isolated from other electrodes and components by a series of spaces or kerfs 216 which may be created by parallel sawing of the transducer components 211 and the rear electrodes 213. Before or after the transducer cells 103 are separated, matching layers may be applied to reconnect the front electrode 214 of the transducer cells 103, so that they have one shared electrode. The transducer cells 103 may, for example, be lead zirconate titanate transducer cells (PZTs), a single crystal material such as lead magnesium niobate-lead titanate (PMN-PT) or lead zinc niobate-lead titanate (PZN-PT), capacitive Micromachined Ultrasonic Transducer cells (cMUTs), piezoelectric Micromachined Ultrasonic Transducer cells (pMUTs), or PolyVinylidine DiFluoride (PVDF) transducer cells.

The ASIC 106 includes a substrate 220, an upper surface 221, a lower surface 222, a circuit region 223, and an Input/Output (I/O) region 224 formed along an edge 232 of the ASIC 106 and extending into the ASIC substrate 220. The I/O region 224 may include I/O circuitry or protection circuitry. The circuit region 223 of the ASIC 106 is formed of an array of like transducer circuit cells, e.g., 227a-227e, each circuit cell 227 having a circuit cell contact 228 (referenced as 228a-228e) along an upper surface 221 of the ASIC 106 and connected to a corresponding lower flex contact pad 244 through a circuit cell bond pad 229. Each circuit cell 227 sends electrical signals to one transducer cell 103 and receives signals from the same transducer cell 103. The I/O region 224 of the ASIC 106 is formed of a plurality of I/O elements 230, each I/O element 230 having an I/O element contact 231 along the upper surface 221 of the ASIC 106, connected through an adjoining I/O bond pad 233 to a lower flex I/O contact pad 246 and along conductive traces within the connector 105 for transmitting signals to and receiving signals from the system console 120 shown in FIG. 1. Individual traces, extending through the connector portion 249-1 and connecting the I/O contact pads 246 to the interconnection structure 107, are not shown in FIG. 3.

The ASICs 106 may be thinned to an overall thickness between 25 and 100 microns to provide a flexible module. Curved arrays formed of flexible modules can provide better imaging quality relative to arrays formed in a flat plane. A curved array may be formed by tiling relatively small modules along a curved surface. That is, the curved array may comprise a series of flat modules formed along a plane with varying angles relative to the plane. The transducer subarrays 104 are attached to the upper surface 241 of flexible circuit assembly 240 with a first layer 271 of anisotropically conductive adhesive, facilitating electrical connection between upper flex contact pads 243 (243a-243e) of the assembly 240 and the transducer contact pads 212. Alternately, electrical connection between upper flex contact pads 243 and transducer contact pads 212 may be formed with solder balls or "chip on flex" or a non-conductive adhesive applied and then subjected to heat and pressure so that the adhesive is displaced as electrical surfaces come into contact with one another. Connections with ASICs may also be accomplished using a standard high density flex based process in which connections to the ASIC may be integrally formed with conductive vias in the flex material, i.e., with the vias providing electrical contact to pads on the ASIC. See, for example, U.S. Pat. No. 5,527,741 incorporated herein by reference.

The ASICs 106 are attached to the lower surface 242 of the circuit assembly 240 with a second layer 272 of anisotropically conductive adhesive, facilitating electrical connection between the lower flex contact pads 244 and the circuit bond pads 229. Alternately, electrical connection between lower flex contact pads 244 and the circuit bond pads 229 may be also formed with solder balls or "chip on flex" or other well-known methods such as Compression Displacement Bonding. The second adhesive layer 272 also effects electrical contacts between the lower flex I/O contact pads 246 and the I/O bond pads 233. In other embodiments, a conductive or nonconductive dematching layer having high acoustic impedance (e.g., >60 MRayls), may be placed between the flexible circuit assembly 240 and the transducer subarray 104. For non-conductive media, vias may be formed through the layers to provide connections between the transducer cells 103 and the circuit assembly 240. It is also contemplated that a backing stack having low acoustic impedance (e.g., <8 MRayls) may be positioned between the transducer cells 103 and the assembly 240.

The flex tail 249-1 of the circuit assembly 240 routes signals from the I/O bond pads 233 of the module 10 to the interconnection structure 107 coupled to an assembly connector portion 290. The interconnection structure 107 receives I/O signals from individual modules 10. Flex tails 249 from other modules 10, for example, 249-n, are also routed to the interconnection structure 107 for connection to the system console 110 (shown in FIG. 1). The I/O bond pads 233 may be formed along multiple edges of each ASIC 106 and connect with other circuitry of the imaging system through multiple flex tails 249 which may be formed along different side edges of the module 10. In other embodiments, each flex tail 249 may route signals from a plurality of modules 10.

The transducer subarray 104 extends along the first plane P11 over both the I/O region 224 and the flex tail 249-1 at a uniform first pitch spacing $a_{11}$. The circuit cells 227 in the ASIC 106 are formed at a second pitch spacing $a_{12}$ along a second plane P12 parallel with the plane P11 such that $a_{12} < a_{11}$. With the pitch spacing $a_{12}$ of the ASIC circuit cells 227 smaller than the pitch spacing $a_{11}$ of the transducer cells 103, each transducer subarray 104 can, as shown, overlie both an ASIC 106 and the flex tail 249-1. This enables tiling of transducer modules 10 to form the large area array transducer assembly 101 with uniformly spaced rows $x_r$ and uniformly spaced columns $y_c$ across the entire assembly 101 such that there are no significant variations in spacings between modules throughout the rows and columns across the assembly 101 and no significant gaps between cells 103 in adjoining subarrays.

With an understanding that the terms vertical and vertically aligned mean an orientation normal to the planes P11 and P12, it can be seen from FIG. 3 that some of the transducer cells 103, such as cell 103a, are vertically aligned with, i.e., overlying, the associated bond pad 229a in the ASIC 106. That is, "vertically aligned with" and "overlying" as used herein mean that a transducer cell such as the cell 103a is aligned along a direction normal to the planes P11 and P12 with the bond pad 229a. In contrast, horizontal offset means a displacement along a horizontal direction which results in features not being vertically aligned. Generally, vertical alignment means that part or all of a first feature, e.g., a cell 103, is vertically aligned with part or all of a second feature, e.g., a pad 229. Other cells, such as the cells 103d and 103e are not vertically aligned with associated bond pads, but rather are horizontally offset such that they do not overlie the bond pads 229d and 229e to which they must be connected in order to effect operation. Reference to a relationship wherein a first feature does not overlie a second feature means that no part of one feature is vertically aligned with any part of the second feature.

In the module 10, some of the transducer cells 103 (e.g., cell 103a) are vertically aligned with respect to the circuit cells 227 (e.g., cell 227a) to which they are connected while horizontal offsets exist between others of the transducer cells 103 (e.g., cell 103d) and associated circuit cells 227 (e.g., cell 227d). Connection between transducer cells 103 and circuit cells 227 that are not vertically aligned with respect to one another is effected with a redistribution system 250 comprising a plurality of conductive paths 245 formed in the flexible circuit assembly 240. Each conductive path 245 provides an electrical connection between an ASIC circuit contact pad 229 and a corresponding transducer contact pad 212.

By way of example, for the transducer cell 103a directly overlying a circuit cell 227a, electrical connection between the transducer cell 103a and the circuit cell 227a is provided via a straight conductive path 245a between the upper flex contact pad 243a and the associated lower flex contact pad 244a. For the transducer cell 103d not directly overlying circuit cell 227d, electrical connection between the transducer cell 103d and the circuit cell 227d is provided via a conductive path 245d in the flexible circuit assembly 240. The conductive path 245d includes a horizontal section 245-H to accommodate the misalignment between the transducer cell 103d and the circuit cell 227d. The exemplary path 245d is illustrative of the redistribution function served by the redistribution system 250 when the pitch $a_{11}$ of the transducer cells 103 differs from the pitch $a_{12}$ of the circuit cells 227. The flexible circuit assembly 240 also provides conductive paths (not shown) between the I/O contacts 231 and the interconnection structure 107.

In the exemplary layout of FIG. 3, the pitch spacing between adjacent lower flex contact pads 244 may, as shown, be uniform and equivalent to the pitch $a_{12}$ between two adjacent circuit cells 227; and the pitch spacing between adjacent upper flex contact pads 243 may be uniform and equivalent to the pitch $a_{11}$ between two adjacent transducer circuit cells 103. More generally, the pitch spacing between adjacent upper flex contact pads 243 need not be uniform and the pitch spacing between adjacent lower contact pads need not be uniform. For example, there may be variable spacing between adjacent pads 243c, 243d, and 243e, each of which is associated with the adjacent conductive paths 245c, 245d, and 245e, which adjacent paths are spaced apart at variable pitch greater than $a_{12}$. The pitch between adjacent transducer contact pads 212 may not be the same as $a_{11}$, the pitch of the transducer cells 103. The above-described arrangements effect connection of each transducer contact pad 212 to a corresponding bond pad 229, while permitting differences in pitch spacings $a_{11}$ and $a_{12}$ to accommodate horizontal offsets between the multiple pairs of transducer cells 103 and circuit cells 227.

Figure 4:
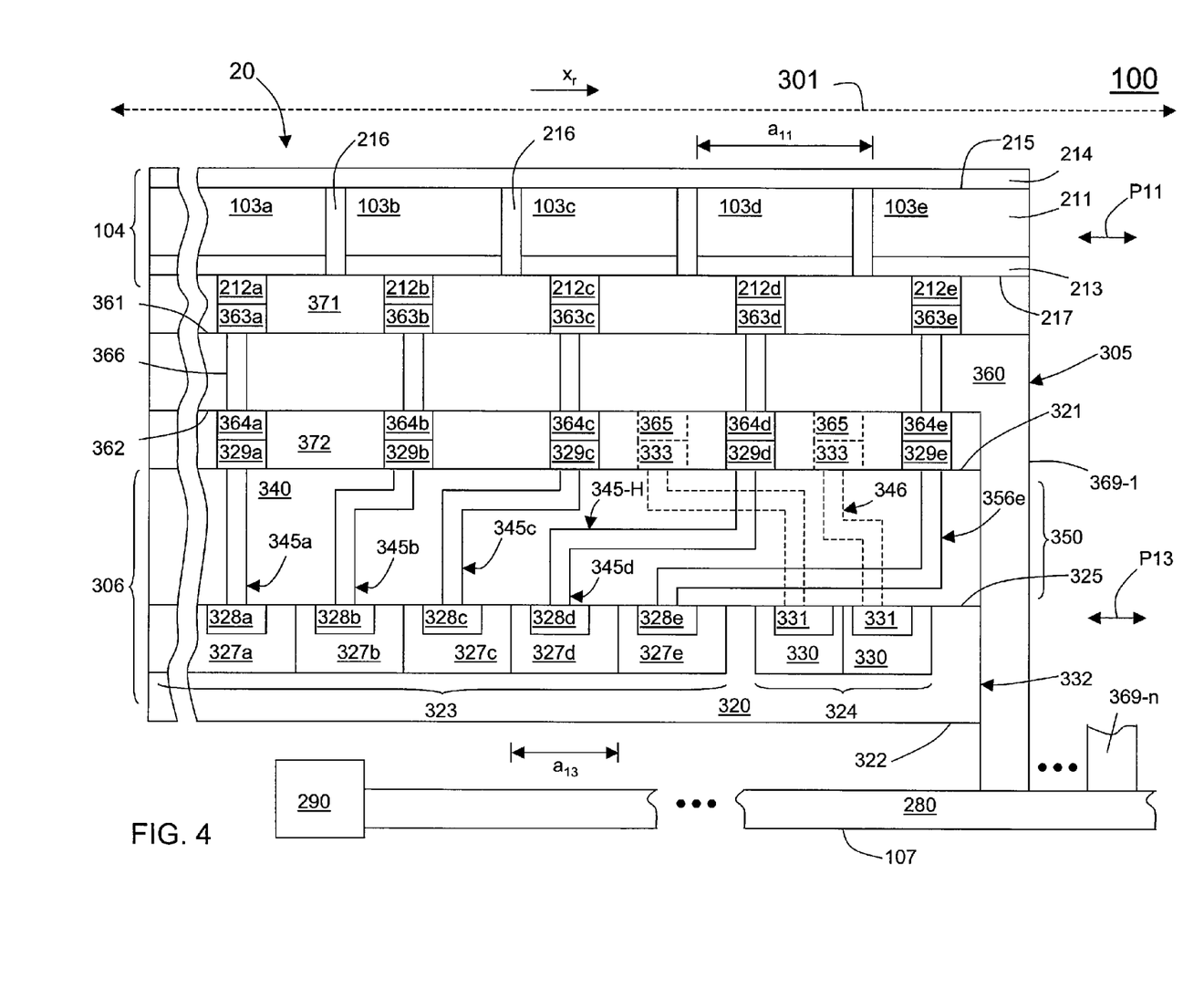
FIG. 4 illustrates in partial cross-sectional view another example of a transducer module.

According to an alternate embodiment, FIG. 4 illustrates a transducer assembly 301 in a partial cross-sectional view of a transducer module 20. The assembly 301 and the module 20 may, respectively, be interchanged with the assembly 101 and the transducer module 10 in the embodiment of FIG. 3. The view of the module 20 is also taken along line A-A' of FIG. 2 and through a row $x_r$ of transducer cells 103 which extends across adjacent modules 20 along the same plane P11 described with reference to FIG. 3. The module 20 comprises the sub-array 104 of transducer cells 103 and the interconnection structure 107 as described with respect to FIG. 3, and a connector 305 and an ASIC 306. The connector 305, formed of a flexible circuit board 360 having an upper surface 361 and a lower surface 362, is functionally similar to the connector 105 of FIG. 3. The connector 305 includes a plurality of upper flex contact pads 363 (e.g, 363a-363e) formed along an upper surface 361 of the flexible circuit board 360, a plurality of lower flex contact pads 364 (e.g, 364a-364e) formed along a lower surface 362 of the circuit board 360, and a plurality of conductive through-flex vias 366 connecting pairs of pads 363 and 364. The connector 305 further includes a plurality of lower flex I/O contact pads 365 for electrically connecting the ASIC 306 to the interconnection structure 107 and a flex tail 369-1 for providing an external connection from the module 20 to the system console 120 (shown in FIG. 1) through the interconnection structure 107. Flex tails from other modules 20, for example, 369-n, are also routed to the interconnection structure 107. The ASIC 306, having a substrate 320, an upper surface 321, a lower surface 322, a circuit region 323, and an I/O region 324 formed along an edge 332 of the ASIC 306, is functionally similar to the ASIC 106 of FIG. 3, but includes a plurality of conductive paths 345 formed in a metallization structure 340 functioning as a redistribution system 350.

The ASIC 306 includes a plurality of like transducer circuit cells 327a-327e formed along a second plane P13 parallel to the plane P11. Each circuit cell 327 having a circuit cell contact 328 (referenced as 328a-328e) along an interface 325 between the ASIC substrate 320 and the metallization structure 340, sends electrical signals to and receives electrical signals from one associated transducer cell 103 via one of several conductive paths 345 (e.g., 345a-345e) formed in the metallization structure 340 overlying the substrate 320 of the ASIC 306. In the I/O region 324, the ASIC 306 also includes a plurality of I/O circuit cells 330, each I/O circuit cell 330 having an I/O contact 331 also formed along the interface 325 between the ASIC substrate 320 and the metallization structure 340. In the exemplary embodiment of FIG. 4, I/O bond pads 333 are formed between the circuit cell bond pads 329 along the upper surface 321 of the ASIC 306. A plurality of conductive paths 346 for I/O connections formed in the metallization structure 340 are illustrated in part and with phantom lines to indicate positioning in a different plane than that plane through which the line A-A' passes. Each I/O circuit contact 331 is connected to an associated I/O bond pad 333 (also in a different plane as indicated with phantom lines) via one of conductive paths 346 for I/O connections. The flexible circuit assembly 360 provides conductive paths (not shown) between the I/O bond pads 333 and the interconnection structure 107 for sending electrical signals to and receiving electrical signals from the system console 120 (shown in FIG. 1). An array of I/O pads 333 may be formed over the metallization structure 340 above the circuit region 323 of the ASIC 306.

In the embodiment of FIG. 4, each transducer contact pad 212 overlies a corresponding bond pad 329 to which it is connected by a through-flex via 366. Each via 366 is a conductive lead connecting a transducer cell 103 to a conductive path 345 in the redistribution system 350. A first layer 371 of anisotropically conductive adhesive facilitates electrical connection between pairs of upper flex contact pads 363 and transducer contact pads 212. A second layer 372 of anisotropically conductive adhesive facilitates electrical connection between the individual lower flex contact pads 364 for circuit cell connection and the corresponding circuit bond pads 329 and facilitates electrical connection between the lower flex I/O contact pads 365 and the I/O bond pads 333.

Transducer cells 103 in the sub-array 104 are formed in rows $x_r$ and columns $y_c$ extending along the plane P11 across the ASIC 306 and the flex tail 369-1 at the uniform first pitch spacing $a_{11}$. The circuit cells 327 in the ASIC 306 are formed at a second pitch spacing, denoted as $a_{13}$ for this embodiment, along the second plane P13 such that $a_{13} < a_{11}$. With the pitch spacing $a_{13}$ of the ASIC circuit cells 327 smaller than the pitch spacing $a_{11}$ of the transducer cells 103, the sub-array 104 of transducer cells 103 overlies the ASIC 306 and the flex tail 369-1. Transducer cells 103 positioned along rows $x_r$ and columns $y_c$ in each module sub-array 104 and in rows $x_r$ and columns $y_c$ extending across adjacent modules 20 have substantially the same pitch spacing with no significant gaps between adjacent modules 20 or between the rows $x_r$ or between the columns $y_c$.

In the module 20, some of the transducer cells 103 (e.g., cell 103a) are vertically aligned with respect to the circuit cells 327 (e.g., cell 327a) while horizontal offsets exist between others of the cells 103 (e.g., cell 103d) and associated circuit cells 327 (e.g., cell 327d) to which connection is made. Connection between transducer cells 103 and circuit cells 327 that are not vertically aligned with respect one another is effected with the redistribution system 350 formed in the ASIC metallization structure 340 having a plurality of conductive paths 345. Each conductive path 345 provides an electrical connection between an ASIC circuit cell contact 328 and a corresponding circuit cell bond pad 329. For the transducer cell 103a directly overlying a circuit cell 327a, electrical connection between the transducer cell 103a and the circuit cell 327a is provided via a straight conductive path 345a between circuit cell contact 328a and the associated bond pad 329a, a lower flex contact pad 364a, a through-flex via 366 connecting an upper flex contact pad 363a and a corresponding lower flex contact pad 364a, and a transducer contact pad 212a. By way of contrast, for the transducer cell 103d not directly overlying circuit cell 327d, electrical connection between the transducer cell 103d and the circuit cell 327d is provided via a conductive path 345d between a circuit cell contact 328d and the associated bond pad 329d, a lower flex contact pad 364d, a through-flex via 366 connecting an upper flex contact pad 363d and a corresponding lower flex contact pad 364d, and a transducer contact pad 212d. The conductive path 345d includes a horizontal section 345-H, i.e., parallel with the plane P11, to accommodate the misalignment between the transducer cell 103d and the circuit cell 327d.

The exemplary path 345d is illustrative of the redistribution function served by the redistribution system 350 (e.g., including the paths 345c, 345d and 345e) in the metallization structure 340 when the pitch $a_{11}$ of the transducer cells 103 differs from the pitch $a_{13}$ of the circuit cells 327. That is, when transducer contact pads 212 cannot vertically overlie bond pads of associated circuitry on the adjoining ASIC 306, the connection can be effected without modifying the uniform distribution of transducer cells 103 in the module 20.

In the exemplary embodiment of FIG. 4, the pitch between adjacent circuit cell contacts 328 may be uniform and equivalent to the pitch $a_{13}$ between two adjacent circuit cells 327. However, the pitch spacing between circuit cell bond pads 329 is greater than $a_{12}$ as evidenced by the pads 329a, 329b, 329c, 329d, and 329e. The pitch between adjacent transducer contact pads 212 may be non-uniform with respect to the transducer cells 103, but in this embodiment is shown to be sufficiently close to the pitch between adjacent circuit cell bond pads 329 to effect vertical alignment between pairs of cells 103 and associated bond pads 329. This enables each transducer contact pad 212 to directly overlie a corresponding bond pad 329 while the redistribution system 350 addresses any offset in pitch spacing between each transducer cell 103 and the circuit cell 327 to which it is connected. In other embodiments multiple layers or structures may each perform part or all of a redistribution function. For example, the flex board 360 may be configured include conductive paths having horizontal offsets similar to those shown for the assembly 240 of FIG. 3 while the redistribution system 350 also provides horizontal offsets.

Figure 5:
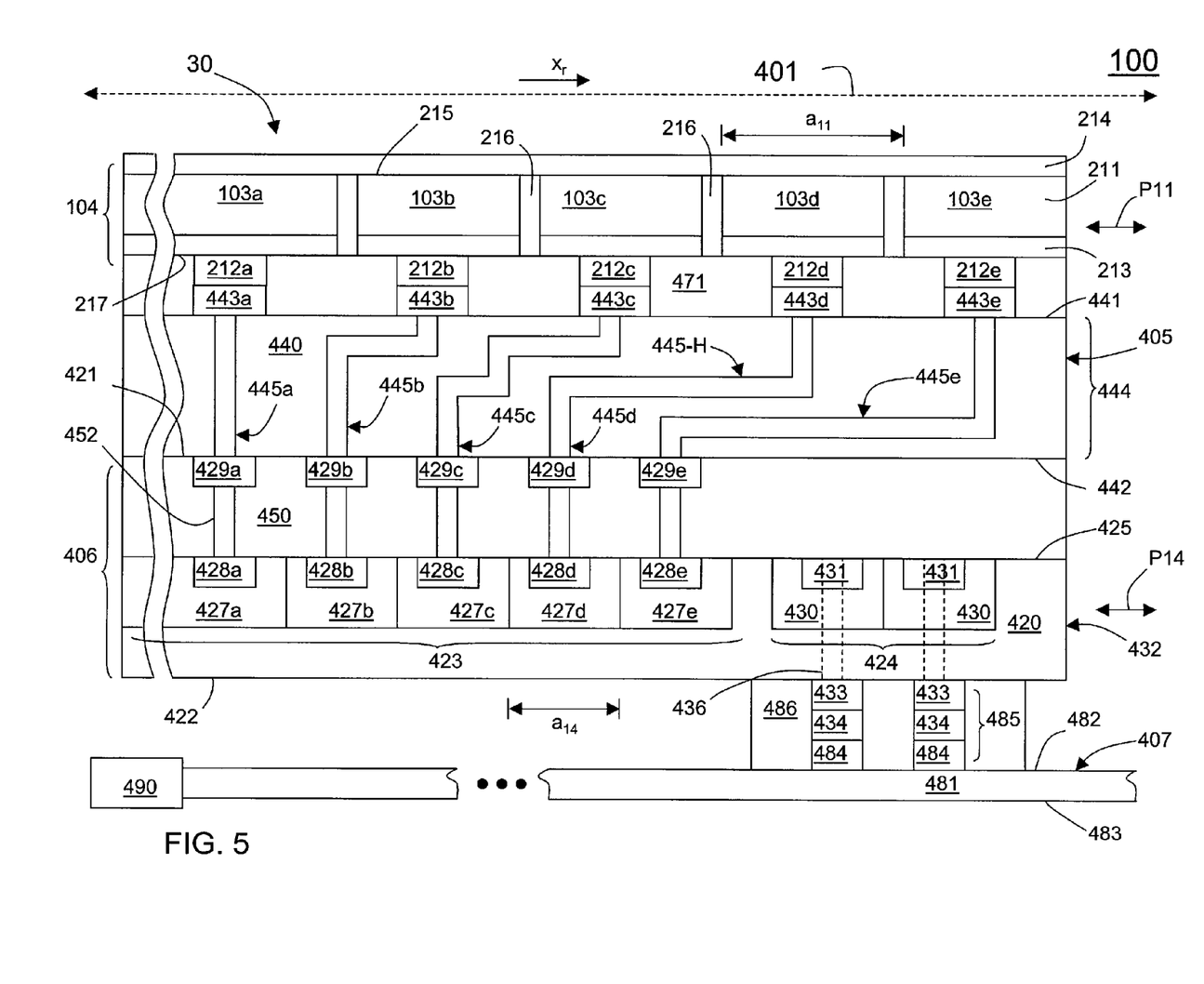
FIG. 5 illustrates in partial cross-sectional view another example of a transducer module.

In the embodiment of FIG. 5 a transducer assembly 401 positionable in the system 100 is illustrated in the partial cross-sectional view of a transducer module 30. The assembly 401 and the module 30 may, respectively, be interchanged with the assembly 101 and the transducer module 10 in FIG. 3. The view of the module 30 is also taken along line A-A' of FIG. 2 and through a row $x_r$ of transducer cells 103 which extends across adjacent modules 30 along the plane P11. In the embodiment of FIG. 5 the transducer module 30 comprises the sub-array 104 of transducer cells 103 as described with respect to FIG. 3, a connector 405, an ASIC 406 having a circuit region 423 and an I/O region 424, and an interconnection structure 407 coupled to an assembly connector portion 490.

The connector 405 is formed of a post-processed metallization structure or a connector metallization structure 440 having an upper surface 441 and a lower surface 442, and is functionally similar to the connector 105 of FIG. 3 but does not incorporate a flex tail. The transducer subarrays 104 are attached to the upper surface 441 of the structure 440 with a first layer 471 of anisotropically conductive adhesive. The connector 405 is formed over the circuit region 423 and extends over the I/O region 424 formed along an edge 432 of the ASIC 406. The connector 405 includes a plurality of upper connector contact pads 443 (e.g, 443a-443e) formed along an upper surface 441 of the connector metallization structure 440 and functions as a redistribution system 444 with a plurality of conductive paths 445 (e.g., 445a-445e) for providing electrical connections between the transducer subarray 104 and the ASIC 406. The conductive paths 445 may be formed with multi-layers of conductive material, for example, copper or aluminum, in a dielectric material such as polyimide or Benzocyclobutene (BCB) which is deposited on an upper surface 421 of the ASIC 406. The transducer cells 103 are attached to the upper surface 441 of the connector metallization structure 440 with a layer 471 of anisotropically conductive adhesive.

The ASIC 406 having a substrate 420, an upper surface 425, and a lower surface 422, is functionally similar to the ASIC 106 of FIG. 3, but includes a series of conductive paths 452 formed in an ASIC metallization structure 450. The interconnection structure 407 is functionally similar to the interconnection structure 107 of FIG. 3, but is connected to the ASIC 406 by bump bonding. The modules 30 are coupled to the interconnection structure 407 to form the transducer assembly 401.

The ASIC 406 further includes a plurality of like circuit cells 427a-427e formed along a second plane P14 parallel to the plane P11. Each circuit cell 427 having a circuit cell contact 428 (428a-428e) along an interface 425 between the ASIC substrate 420 and the ASIC metallization structure 450, sends electrical signals to and receives electrical signals from one associated transducer cell 103 via one of several conductive paths 445 (e.g., 445a-445e) formed in the connector metallization structure 440 overlying the substrate 420 of the ASIC 406. In the I/O region 424, the ASIC 406 includes a plurality of I/O cells 430, each I/O cell having an I/O cell contact 431 also formed along the substrate surface 425. The ASIC metallization structure 450 includes a plurality of circuit cell contact pads 429 formed along the ASIC upper surface 421. Each vertical conductive path 452 in the ASIC metallization structure 450 provides an electrical connection between each circuit cell contact 428 and an associated cell contact pad 429. In other embodiments, the conductive paths 452 between pairs of circuit cell contacts 428 and corresponding circuit cell contact pads 429 may be formed with horizontal offsets.

In the I/O region 424 of the ASIC 406, a plurality of through-die vias 436 are formed. Each through-die via 436 is filled or plated with a conductive material such as copper, and an under-bump metal pad 433 is formed at each via along the lower surface 422 of the ASIC 406. The through-die vias 436 are shown in phantom lines because they may be in a different plane than that passing through the line A-A'. Solder bumps 434 are formed over the under-bump metal pads 433. The interconnection structure 407 is a large area flexible circuit board 481 having an upper surface 482 and a lower surface 483. It includes a plurality of flex contact pads 484 formed on the upper surface 482. Electrical contacts between the I/O contact pads 433 and the flex contact pads 484 are made by bump bonding, forming bonded pads 485. A layer 486 of dielectric adhesive is provided around the bonded pads 485. The board 481, coupled to the connector portion 490, provides electrical connections between individual modules 30 and the system console 120 shown in FIG. 1. In other embodiments the interconnection structure 407 may comprise a circuit board structure such as a glass substrate coated with an amorphous silicon layer, a polyimide substrate, a ceramic substrate, or a printed circuit board.

In the module 30, some of the transducer cells 103 (e.g., cell 103a) are vertically aligned with respect to the circuit cells 427 (e.g., cell 427a) while horizontal offsets exist between others of the cells 103 (e.g., cell 103d) and associated circuit cells 427 (e.g., cell 427d). Connection between transducer cells 103 and circuit cells 427 that are not vertically aligned with respect to one another is effected with the redistribution system 444 formed in the post-processed metallization structure 440 having multiple conductive paths 445.

Each conductive path 445 provides an electrical connection between a connector contact pad 443 and a corresponding circuit cell bond pad 429. For the transducer cell 103a directly overlying a circuit cell 427a, electrical connection between the transducer cell 103a and the circuit cell 427a is provided via a circuit cell contact 428a, a conductive path 452 in the ASIC metallization structure 450, a circuit cell bond pad 429a, a straight conductive path 445a between a connector contact pad 443a and the circuit cell bond pad 429a, the connector contact pad 443a and a transducer contact pad 212a. For the transducer cell 103d not directly overlying circuit cell 427d, electrical connection between the transducer cell 103d and the circuit cell 427d is provided via a circuit cell contact 428d, a conductive path 452 in the ASIC metallization structure 450, a circuit cell bond pad 429d, a conductive path 445d between a connector contact pad 443d and the circuit cell bond pad 429d, the connector contact pad 443d and a transducer contact pad 212d.

The conductive path 445d includes a horizontal section 445-H, i.e., parallel with the plane P11, to accommodate the misalignment between the transducer cell 103d and the circuit cell 427d. The exemplary path 445d is illustrative of the redistribution function served by the redistribution system 444 (e.g., including the paths 445c, 445d and 445e) in the post-processed metallization structure 440 when the pitch $a_{11}$ of the transducer cells 103 differs from the pitch $a_{14}$ of the circuit cells 427. That is, when transducer contact pads 212 cannot overlie bond pads of associated circuitry on the adjoining ASIC 406, the connection can be effected without modifying the uniform distribution of transducer cells 103 in the module 30.

The transducer cells 103 in each sub-array 104 are formed in rows $x_r$ and columns $y_c$ extending along a first plane P11, over the circuit region 423 and over the I/O region 424 at the uniform first pitch spacing $a_{11}$. The circuit cells 427 in the ASIC 406 are formed at the second pitch spacing, $a_{14}$, along a second plane P14 parallel to the plane P11 such that $a_{14} < a_{11}$. With a pitch spacing $a_{14}$ for the ASIC circuit cells 427 that is smaller than the pitch spacing $a_{11}$ of the transducer cells 103, the sub-array 104 of transducer cells 103 can nonetheless overlie both the circuit region 423 and the I/O region 424. Transducer cells 103 positioned along rows and columns in each sub-array 104 and in rows and columns extending across adjacent modules 30 have substantially the same pitch spacing with no significant gaps between adjacent modules.

The redistribution system 444 comprises a plurality of conductive paths 445 formed in the post-processed metallization structure 440. Each conductive path 445 provides an electrical connection between an ASIC circuit cell contact pad 429 and a corresponding connector contact pad 443. By way of example, for a transducer cell 103a directly overlying a circuit cell 427a, electrical connection between the transducer cell 103a and the circuit cell 427a is provided via a vertical conductive path 445a between the circuit cell contact pad 429a and the associated conductor contact pad 443a. For the transducer cell 103d, not directly overlying circuit cell 427d, electrical connection between the transducer cell 103d and the circuit cell 427d is provided via a conductive path 445d between circuit cell contact pad 429d and the associated conductor contact pad 443d. The conductive path 443d includes a horizontal section 445-H, i.e., parallel with the plane P11, to accommodate the misalignment between the transducer cell 103d and the circuit cell 427d.

Figure 6:
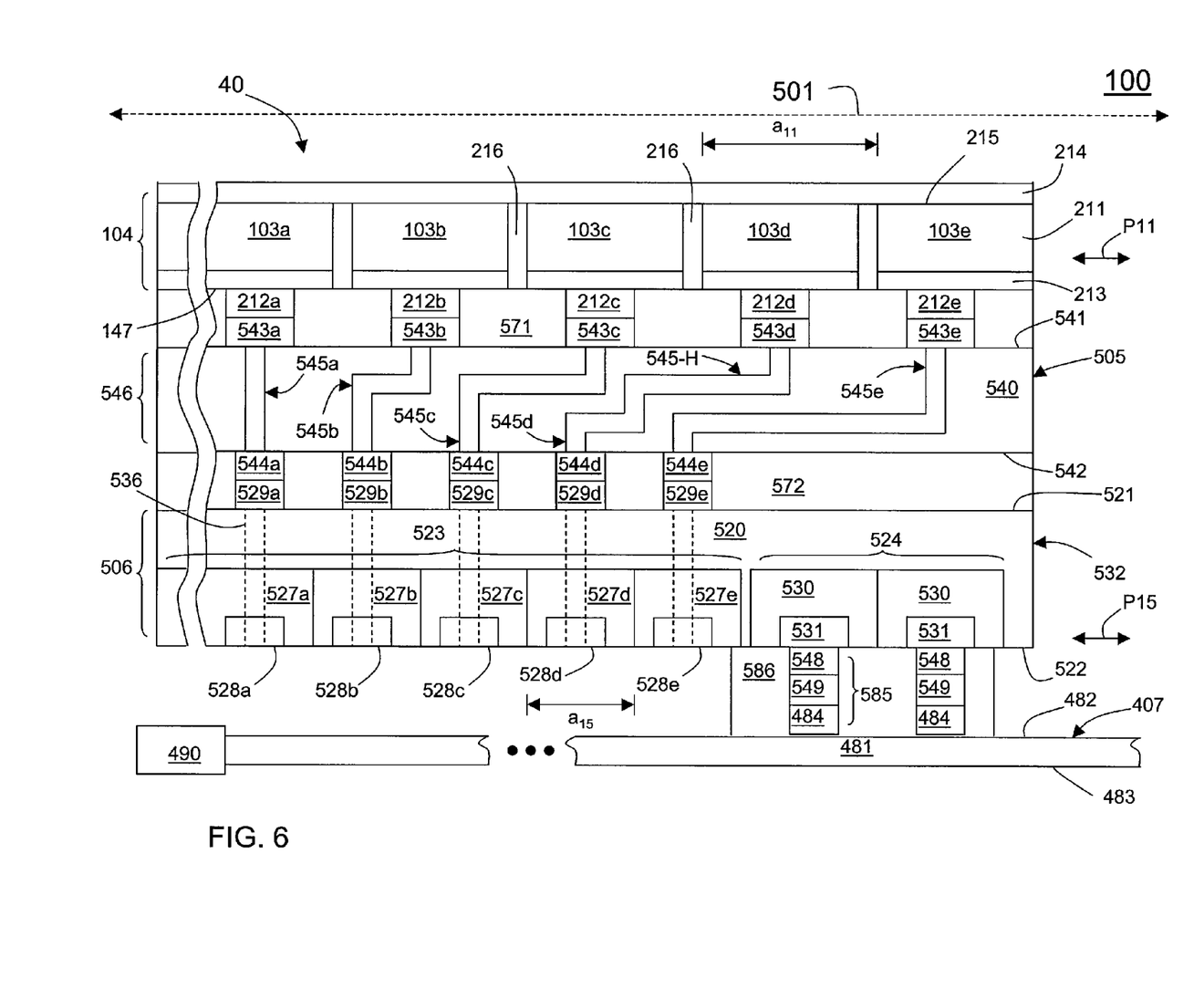
FIG. 6 illustrates in partial cross-sectional view another example of a transducer module.

In FIG. 6 another exemplary embodiment of a transducer assembly 501 in the system 100 is illustrated in the partial cross-sectional view of a module 40. The assembly 501 and the module 40 may, respectively, be interchanged with the assembly 101 and the transducer module 10 in FIG. 3. The view of the module 40 is taken along line A-A' of FIG. 2 and through a row $x_r$ of transducer cells 103 which extends across adjacent modules 40 along the plane P11. The transducer module 40 comprises the sub-array 104 of transducer cells 103 as described with reference to FIG. 3 and the interconnection structure 407 as described with respect to FIG. 5, a connector 505, and an ASIC 506 having a circuit region 523 and an I/O region 524. The connector 505, formed of an interposer 540 having an upper surface 541 and a lower surface 542, is functionally similar to the connector 105 of FIG. 3, but does not incorporate a flex tail.

The transducer subarrays 104 are attached to the upper surface 541 of the interposer 540 with a first layer 571 of anisotropically conductive adhesive. The connector 505 includes a plurality of upper interposer contact pads 543 (e.g, 543a-543e) formed along an upper surface 541 of the interposer 540, a plurality of lower interposer contact pads 544 (e.g, 544a-544e) formed along a lower surface 542 of the interposer 540, and a plurality of conductive paths 545 (e.g., 545a-545e) for connecting pairs of pads 543 and 544. The interposer 540 serves as a redistribution system 546 with multiple conductive paths 545 providing electrical connections between the ASIC 506 and the corresponding transducer subarray 104. The ASIC 506 having a substrate 520, an upper surface 521, and a lower surface 522 is functionally similar to the ASIC 106 of FIG. 3, but includes a circuit region 523 and an I/O region 524 formed along the lower surface 522 of the ASIC 506. The modules 40 are coupled to the interconnection structure 407 to form the transducer assembly 501. The connector 505 and the redistribution system 546 may be formed of a flexible circuit assembly comprising one or more flexible circuits and may also provide electrical connections between the adjacent ASICs 506.

The transducer cells 103 are attached to the upper surface 541 of the interposer 540 with a first layer 571 of anisotropically conductive adhesive and the upper surface 521 of the ASIC 506 is attached to the lower surface 542 of the interposer 540 with a second layer 572 of anisotropically conductive adhesive. The ASIC 506, having a plurality of circuit cells 527 in a circuit region 523 and a plurality of I/O circuit cells 530 in an I/O region 524 formed along an edge 532 of the ASIC 506, also includes a series of through-die vias 536 filled or plated with conductive material such as copper. The conductive through-die vias 536 are shown in phantom lines as they are in a different plane than that passing through the line A-A'.

In each circuit cell 527 a circuit cell contact 528 formed along the lower surface 522 of the ASIC 506 is coupled through a via 536 to a corresponding backside contact pad 529 formed along the upper surface 522 of the ASIC 506. In the I/O region 524 a plurality of I/O contacts 531 are formed along the lower surface 522 of the ASIC 506.

The interconnection structure 407 is formed of a large area flexible circuit board 481 having a plurality of flex contact pads 484 formed on the upper surface 482 thereof as described with reference to FIG. 5. Electrical contacts between individual I/O contacts 531 and the corresponding flex contact pads 484 are made by bump bonding. An under-bump metal pad 548 is formed on each I/O contact 531 and a solder bump 549 is formed on each under-bump metal pad 548. Bonding between the solder bumps 549 and flex contact pads 484 is effected with heat and compression, forming bonded pads 585. A dielectric adhesive 586 is provided around the bonded pads 585. The bond pads 585 are, generally, multilevel metal bond pad stacks. Connections between the interposer 540 and the ASIC 506 can also be effected with bump bonding. That is, the contacts 529 may be formed as under bump metal pads with solder bumps 549 formed thereon. Bonding between the solder bumps formed on the contacts 529 and the interposer contact pads 544 is effected with heat and compression to form a multilevel metal bond pad stack.

As illustrated in other embodiments, the sub-array 104 of transducer cells 103 is formed in rows and columns extending along a first plane P11, over the circuit region 523 and over the I/O region 524 at a uniform first pitch spacing $a_{11}$. The circuit cells 527 in the ASIC 506 are formed at a second pitch spacing, denoted $a_{15}$ for this embodiment, along a second plane P15 parallel to the plane P11 such that $a_{15} < a_{11}$. With the pitch spacing $a_{15}$ of the ASIC circuit cells 527 smaller than the pitch spacing $a_{11}$ of the transducer cells 103, the sub-array 104 of transducer cells 103 overlies the circuit region 523 and the I/O region 524, thereby allowing for tiling without significant gaps.

In the module 40, some of the transducer cells 103 (e.g., cell 103*a*) are vertically aligned with respect to the circuit cells 527 (e.g., cell 527*a*) while horizontal offsets exist between others of the cells 103 (e.g., cell 103*d*) and associated circuit cells 527 (e.g., cell 527*d*). Connection between transducer cells 103 and circuit cells 527 that are not vertically aligned with respect to one another is effected with the redistribution system 546 formed in the interposer 540 and having multiple conductive paths 545. Each conductive path 545 provides an electrical connection between an upper interposer contact pad 543 and a lower interposer contact pad 544. For the transducer cell 103*a* directly overlying a circuit cell 527*a*, electrical connection between the transducer cell 103*a* and the circuit cell 527*a* is provided via a circuit cell contact 528*a*, a conductive through die via 536 in the ASIC 506, a backside bond pad 529*a*, a lower interposer contact pad 544*a*, a straight conductive path 545*a* between an upper interposer contact pad 543*a* and the lower interposer contact pad 544*a*, the upper interposer contact pad 544*a*, and a transducer contact pad 212*a*.

For the transducer cell 103*d* not directly overlying circuit cell 527*d*, electrical connection between the transducer cell 103*d* and the circuit cell 527*d* is provided via a circuit cell contact 528*d*, a conductive through die via 536 in the ASIC 506, a backside bond pad 529*d*, a lower interposer contact pad 544*d*, a conductive path 545*d* between an upper interposer contact pad 543*d* and the lower interposer contact pad 544*d*, the upper interposer contact pad 544*d*, and a transducer contact pad 212*d*. The conductive path 545*d* includes a horizontal section 545-H, i.e., parallel with the plane P11, to accommodate the misalignment between the transducer cell 103*d* and the circuit cell 527*d*. The exemplary path 545*d* is illustrative of the redistribution function served by the redistribution system 546 (e.g., including the paths 545*c*, 545*d* and 545*e*) in the interposer 540 when the pitch all of the transducer cells 103 differs from the pitch $a_{15}$ of the circuit cells 527. That is, when transducer contact pads 212 cannot overlie bond pads of associated circuitry on the adjoining ASIC 506, the connection can be effected without modifying the uniform distribution of transducer cells 103 in the module 40.

In the example layout of FIG. 6, the pitch spacing between adjacent lower interposer contact pads 544 is uniform and equivalent to the pitch $a_{15}$ between two adjacent circuit cells 527. The pitch spacing between adjacent upper interposer contact pads 543 is uniform and equivalent to the pitch $a_{11}$ between two adjacent transducer cells 123. In other embodiments, the pitch spacing between the upper interposer contact pads 543 may be non-uniform to increase design flexibility. The above-described arrangements effect the vertical alignment of each transducer contact pad 212 with respect to a corresponding bond pad 529, and appropriate changes in pitch spacings to accommodate horizontal offsets between the multiple pairs of transducer cells 103 and circuit cells 527.

Figure 7:
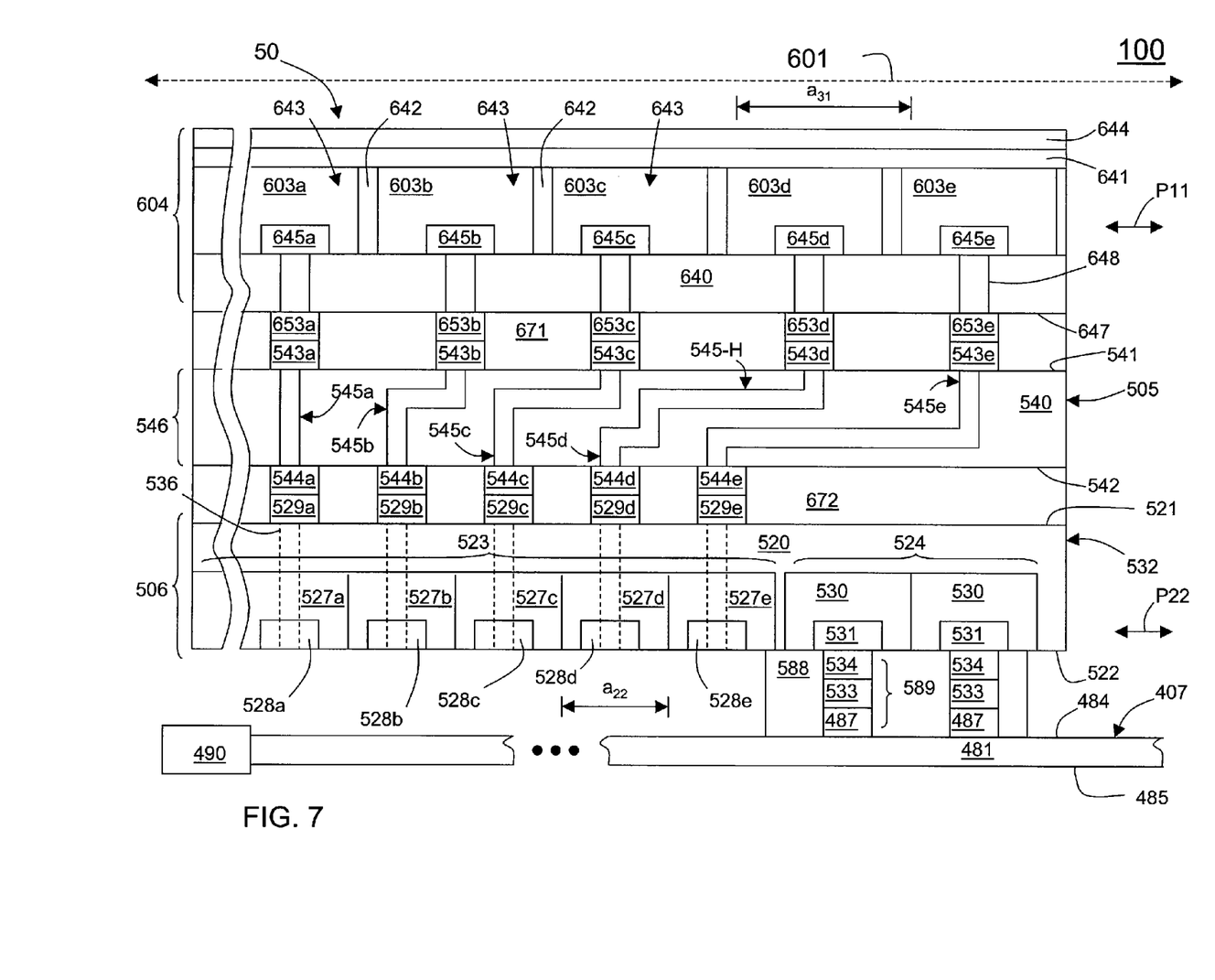
FIG. 7 illustrates in partial cross-sectional view yet another example of a transducer module according to the invention.

In the partial cross-sectional view of FIG. 7 a module 50 in a transducer assembly 601 is illustrated according to another exemplary embodiment. The assembly 601 and the module 50 may, respectively, be interchanged with the assembly 101 and the transducer module 10 in FIG. 3. In the embodiment of FIG. 7, the module 50 comprises the interconnection structure 407, the ASIC 506, and the connector 505 as described with respect to FIG. 6, and a sub-array 604 of transducer cells 603. The view of the module 50 is also taken along line A-A' of FIG. 2 and through a row $x_r$ of transducer cells 603 which extends across adjacent modules 50 along a plane P11. The connector 505, formed with a module 540, is shown to make electrical contacts through mated pairs of interposer pads 544 and backside bond pads 529 in a layer 572 of anisotropically conductive adhesive. Alternately, as described with reference to FIG. 6, connections between the interposer 540 and the ASIC 506 can also be effected with bump bonding wherein the contacts 529 are formed as under bump metal pads with solder bumps 549 formed thereon.

The sub-array 604 of transducer cells 603 is functionally similar to the subarray 104 of transducer cells 103 in FIG. 3, but the transducer cells 603 in FIG. 7 are cMUT transducer elements. An array of such cMUT transducer cells 603 is typically fabricated on a transducer substrate 640 having a lower surface 647, which may, for example, be formed from a wafer of heavily doped silicon. For each cMUT transducer cell 603, a thin membrane or diaphragm 641, e.g., a layer of silicon nitride or silicon, is suspended above the substrate 640. The membrane 641 is supported by insulating supports 642, which may be made of silicon oxide or silicon nitride. The cavities 643 between the membrane 641 and the substrate 640 may be air- or gas-filled or wholly or partially evacuated. A film or layer of conductive material, such as an aluminum alloy or other suitable conductive material, forms a front electrode 644 on the membrane 641, and another film or layer made of conductive material is patterned to form transducer bottom electrodes 645 on the substrate 640. Alternately, the bottom electrodes can be formed by appropriate doping of the semiconductor substrate 640. As shown in FIG. 7, a single cMUT cell can make up the transducer cell, but it is also possible to configure multiple cMUT cells with multiple peripheral supports 642 within the space otherwise allotted to a single transducer cell 603. In the case of configuring multiple cMUT cells within the space otherwise allotted to a single transducer cell 603, a single through via 648 could supply all of the cMUT cells within the area of a single transducer cell 603.

A plurality of through vias 648 are formed in the transducer substrate 640 and filled with conductive material such as aluminum or copper. A plurality of transducer contact pads 653 are formed along a lower surface 647 of the transducer substrate 640. The through vias 648 formed in the transducer substrate 640 each provide an electrical connection between a cMUT transducer bottom electrode 645 and a corresponding transducer contact pad 653.

Figure 8:
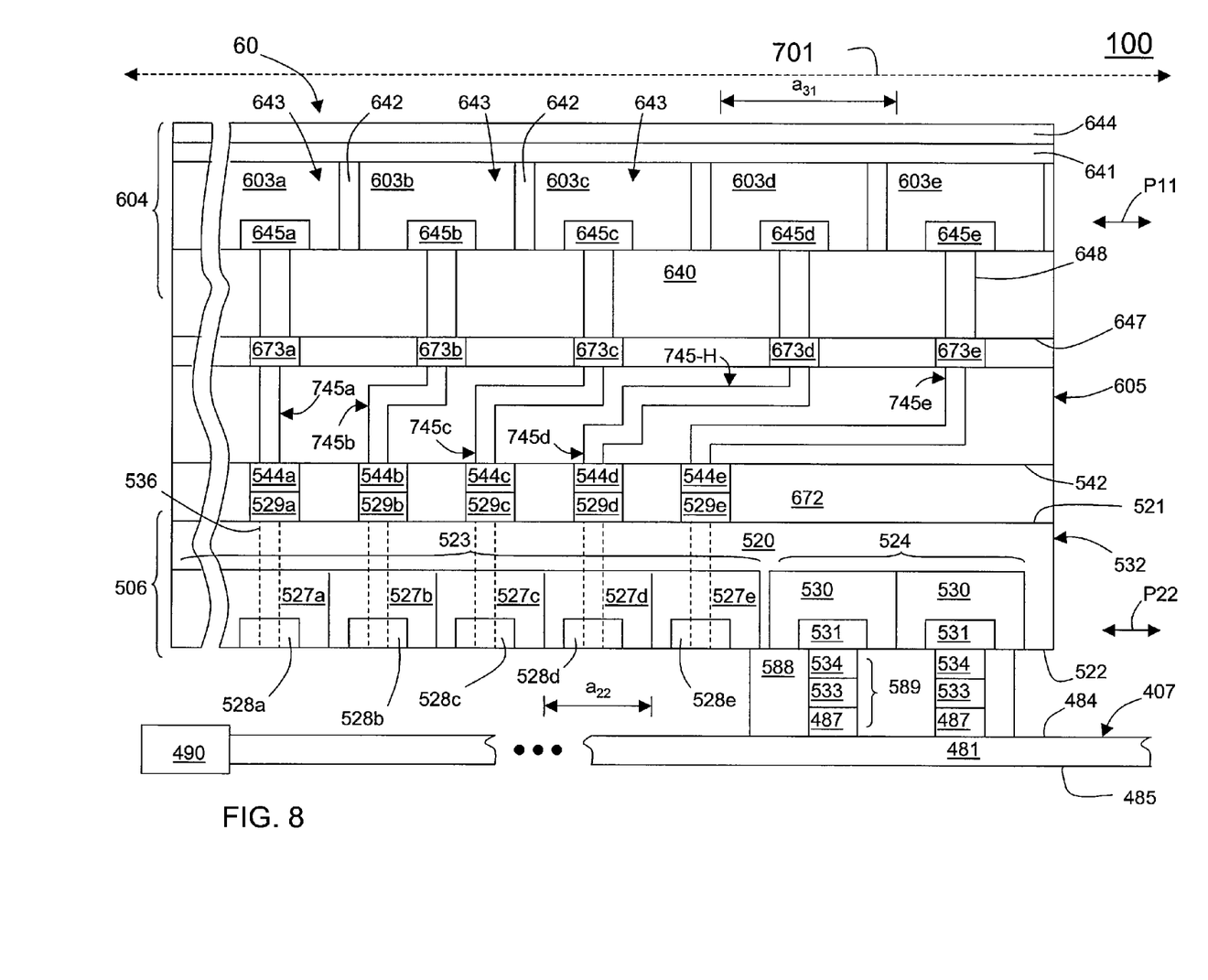
FIG. 8 illustrates in partial cross-sectional view still another example of a transducer module according to the invention.

In the partial cross-sectional view of FIG. 8 a module 60 in a transducer assembly 701 is illustrated according to another exemplary embodiment. The assembly 701 and the module 60 may, respectively, be interchanged with the assembly 101 and the transducer module 10 in FIG. 3. In the embodiment of FIG. 8, the module 60 comprises the interconnection structure 407, the ASIC 506, and the cMUT transducer cells 603 as described with respect to FIG. 7. A connector 605 is formed along a sub-array 604 of the transducer cells 603. The view of the module 60 is also taken along line A-A' of FIG. 2 and through a row $x_r$ of cMUT transducer cells 603 which extends across adjacent modules 60 along a plane P11. In this example, the connector 605 is integrated with the cMUT transducer cells on the semiconductor substrate 640.

A film or layer of conductive material, such as an aluminum alloy or other suitable conductive material, forms a front electrode 644 on the membrane 641, and another film or layer made of conductive material is patterned to form transducer bottom electrodes 645 on the substrate 640. Alternately, the bottom electrodes can be formed by appropriate doping of the semiconductor substrate 640. As shown in FIG. 8, a single cMUT cell can make up the transducer cell, but it is also possible, as discussed with respect to FIG. 7, to configure multiple cMUT cells with multiple peripheral supports 642 within the space otherwise allotted to a single transducer cell 603.

A plurality of through vias 648 are formed in the transducer substrate 640 and filled with conductive material such as aluminum or copper. A plurality of capture pads 673 may be formed along a lower surface 647 of the transducer substrate 640. The through vias 648 formed in the transducer substrate 640 each provide an electrical connection between a cMUT transducer bottom electrode 645 and a corresponding transducer capture pad 673.

The connector 605 is functionally similar to the connector 505 of FIG. 7, but is formed as an interconnect structure, e.g., multi-level metallization, over the lower surface 647 of the transducer substrate 640. The connector 605 is shown to make electrical contacts between each capture pad 673 and a connector bond pad 544. Pairs of the bond pads 544 and backside ASIC bond pads 529 are coupled within a layer 672 of anisotropically conductive adhesive. Alternately, as described with reference to FIG. 6, connections between the connector 605 and the ASIC 506 can also be effected with bump bonding wherein the contacts 529 are formed as under bump metal pads with solder bumps 549 formed thereon.

In the module 60, some of the transducer cells 603 (e.g., cell 603a) are vertically aligned with respect to the circuit cells 527 (e.g., cell 527a) while horizontal offsets exist between others of the cells 603 (e.g., cell 603d) and associated circuit cells 527 (e.g., cell 527d). Connection between transducer cells 603 and circuit cells 527 that are not vertically aligned with respect to one another is effected with the redistribution system 605 having multiple conductive paths 745. Each conductive path 745 provides an electrical connection between a capture pad 673 and a contact pad 544. The transducer cell 603a directly overlies a circuit cell 527a to which it is electrically connected. The transducer cell 603d does not directly overlie the circuit cell 527d to which it is connected. The conductive path 745d includes a horizontal section 745-H, i.e., parallel with the plane P11, to accommodate the misalignment between the transducer cell 603d and the circuit cell 527d. The exemplary path 745d is illustrative of the redistribution function served by the interconnect structure connector 605 (e.g., including the paths 745c, 745d and 745e) when the pitch $a_{31}$ of the transducer cells 603 differs from the pitch $a_{22}$ of the circuit cells 527. That is, when transducer contact pads cannot overlie bond pads of associated circuitry on the adjoining ASIC 506, the connection can be effected without modifying the uniform distribution of transducer cells 103 in the module 60.

The above-described arrangements effect the vertical alignment of each transducer contact pad 212 with respect to a corresponding bond pad 529, and appropriate changes in pitch spacings to accommodate horizontal offsets between the multiple pairs of transducer cells 103 and circuit cells 527.

Manufacture of large area array transducer assemblies can be simplified by a modular design. A large number of modules 10 can share power lines and digital programming bus lines as well as a large number of analog signal channels. These power and signal lines can be bussed out by bump bonding to an interconnection structure 407 formed of a suitable large area substrate 481 such as a flexible circuit board, as illustrated in the embodiments of FIGS. 5, 6, and 7. The power and signal lines may also be bussed out on a glass amorphous-silicon panel, or a standard printed circuit board. The ASICs 106 may be thinned to an overall thickness between 25 microns and 100 microns or more to provide a flexible module. A large area transducer module assembly 101 comprising a plurality of flexible modules 10 including thinned ASICs 106 is suitable for curved arrays for general imaging.

While numerous embodiments of the invention have been illustrated and described, the invention is not so limited. Numerous modifications, variations, substitutions and equivalents will occur to those skilled in the art without departing from the spirit and scope of the present invention as described in the claims.

We claim:

1. An ultrasonic monitoring system comprising a probe unit including:
an array of transducer cells arranged in rows and columns and formed along a first plane with a first pitch along a first direction;
an integrated circuit including an array of circuit cells formed along a second plane parallel to the first plane, the circuit cells spaced apart along the first direction at a second pitch smaller than the first pitch, a first of the transducer cells vertically aligned, along a direction normal to one of the planes, with a first of the circuit cells and having a connection thereto, and a second of the transducer cells offset from vertical alignment with respect to the position of a second circuit cell so as to not overlie the second circuit cell;
a connection subsystem positioned between the array of transducer cells and the array of circuit cells, configured to form the connection of the first transducer cell to the first circuit cell and to connect the second transducer cell with the second circuit cell; and
an interconnection structure positioned to provide electrical connections between the integrated circuit and processing circuitry.

2. The system of claim 1 wherein a portion of the connector subsystem and the circuit cells are formed as part of the same integrated circuit structure.

3. The system of claim 1 further including processing circuitry connected to the integrated circuit through the interconnection structure.

4. The system of claim 1 further including a system console connected to the probe unit through the interconnection structure.

5. The system of claim 4 further including processing circuitry positioned in the console and wherein information is transferable between the probe unit and the system console via a cable coupled between a probe unit line connector in the probe unit and a console line connector in the system console.

6. The system of claim 1, the connection subsystem comprising a connector including a plurality of connector conductive leads and a redistribution system including a second plurality of redistribution system conductive leads, wherein:
a first of the connector conductive leads connects the first transducer cell and a first of the redistribution system conductive leads, and a second of the connector conductive leads connects the second transducer cell and a second of the redistribution system conductive leads,
with the first of the redistribution system conductive leads electrically connected to the first circuit cell and the second of the redistribution system conductive leads electrically connected to the second circuit cell.

7. The system of claim 1 wherein the probe unit is configured with an array of transducer modules, each module comprising a subarray of the transducer cells and a subarray of the circuit cells.

8. The system of claim 1 further including an array of I/O pads formed along an edge of the integrated circuit.

9. The system of claim 7 further including an array of I/O pads with at least one of the I/O pads overlying one of the circuit cells.

10. The system of claim 1 further including a plurality of I/O pads formed along an edge of the integrated circuit and one or more additional I/O pads each overlying or formed directly above one of the circuit cells.

11. The system of claim 1 wherein the connection subsystem comprises a flexible circuit assembly having one or more conductive paths to route an electrical connection between the second transducer cell and the second circuit cell.

12. The system of claim 11 wherein the flexible circuit assembly includes a flexible connector portion for routing an electrical connection between the integrated circuit and the interconnection structure.

13. The system of claim 12 wherein the flexible circuit assembly includes a flexible connector portion for routing an electrical connection between the transducer cells and the interconnect structure.

14. The system of claim 1 wherein the connection subsystem comprises one or more patterned metal layers in the integrated circuit structure providing a connection between the second transducer cell and the second circuit cell.

15. The system of claim 1 wherein the connection subsystem includes a flexible circuit assembly comprising one or more flexible circuits to route a connection between the second cell and the second circuit cell.

16. The system of claim 1 wherein the connection subsystem comprises an interposer having a plurality of conductive paths including a path for routing a connection between the second transducer cell and the second circuit cell.

17. The system of claim 16 wherein the interposer is formed with a semiconductor substrate.

18. The system of claim 16 wherein the interposer is formed of a flexible circuit assembly comprising one or more flexible circuits.

19. The system of claim 16 wherein the interconnection structure comprises a flexible circuit board coupled to a plurality of transducer modules, each comprising transducer cells, to effect electrical connections between the modules and signal processing and control circuitry in the console.

20. The system of claim 16 wherein the interconnection structure comprises a rigid substrate coupled to a plurality of the transducer modules to effect electrical connections between the modules and transmit and receive signal processing and control circuitry in the console.

21. The system of claim 20 wherein the rigid substrate is one selected from a group consisting of a glass substrate coated with an amorphous silicon layer, a polyimide substrate, and a printed circuit board.

22. The system of claim 1 wherein the connection subsystem comprises a flexible circuit assembly formed of one or more flexible circuits for routing electrical connections between adjacent integrated circuit structures.

23. The system of claim 1 wherein the transducer cells are cMUT cells formed along one or more semiconductor layers.

24. The system of claim 7 wherein each subarray of the transducer cells comprises a plurality of cMUT transducer cells formed over a semiconductor layer, said layer including a surface over which a metallization structure is formed to electrically connect each transducer cell to one of the circuit cells.

* * * * *

UNITED STATES PATENT AND TRADEMARK OFFICE
CERTIFICATE OF CORRECTION

PATENT NO.       : 7,892,176 B2
APPLICATION NO.  : 11/743391
DATED            : February 22, 2011
INVENTOR(S)      : Wodnicki et al.

It is certified that error appears in the above-identified patent and that said Letters Patent is hereby corrected as shown below:

On the Title page, item (75), under "Inventors", in Column 1, Line 5, delete "Nishkayuna," and insert -- Niskayuna, --, therefor.

In Column 14, Line 25, delete "all" and insert -- $a_{11}$ --, therefor.

In Column 17, Line 41, in Claim 6, delete "a second" and insert -- a --, therefor.

Signed and Sealed this
Third Day of May, 2011

David J. Kappos
*Director of the United States Patent and Trademark Office*